United States Patent [19]

Grushkin

[11] 4,244,364
[45] Jan. 13, 1981

[54] COMBINATION INTRA-VEINOUS FLOW-METER AND LOW LEVEL FLUID MECHANISM

[76] Inventor: Harold Grushkin, 25 Atlantic Ave., Nanuet, N.Y. 10954

[21] Appl. No.: 14,639

[22] Filed: Feb. 23, 1979

[51] Int. Cl.³ ............................................. A61M 5/14
[52] U.S. Cl. ...................... 128/214 E; 128/DIG. 13; 222/67; 340/624
[58] Field of Search ........... 128/214 R, 214 C, 214 E, 128/214.2, DIG. 13; 222/67; 340/624

[56] References Cited

U.S. PATENT DOCUMENTS

| | | | |
|---|---|---|---|
| 2,850,211 | 9/1958 | Fernandez | 222/67 |
| 3,553,583 | 1/1971 | Wiley | 128/DIG. 13 |
| 3,631,437 | 12/1971 | Campbell et al. | 128/DIG. 13 |
| 3,942,526 | 3/1976 | Wilder et al. | 128/214 E |
| 4,014,010 | 3/1977 | Jinotti | 128/214 E X |

Primary Examiner—Dalton L. Truluck

[57] ABSTRACT

This combination device consists primarily of a stem with a pointed float with plate means at one end, which is freely received in an opaque walled sensing chamber, that removably receives a sensing plug, which is attached to an alerting device, for indicating the ceasing of flow, of intra-venous fluid to a patient. The pointed float also serves as a means, for easy insertion of the flow-meter stylus of the assembly, during insertion, into a bottle of intra-venous fluid. The sensing plug includes a pair of prongs, one of which, has a light emitting diode therein, and the other prong includes a photo-sensitive transistor, and the plate end of the float stem, when lowered between the prongs by low fluid level, will activate the circuitry of an alerting device.

4 Claims, 3 Drawing Figures

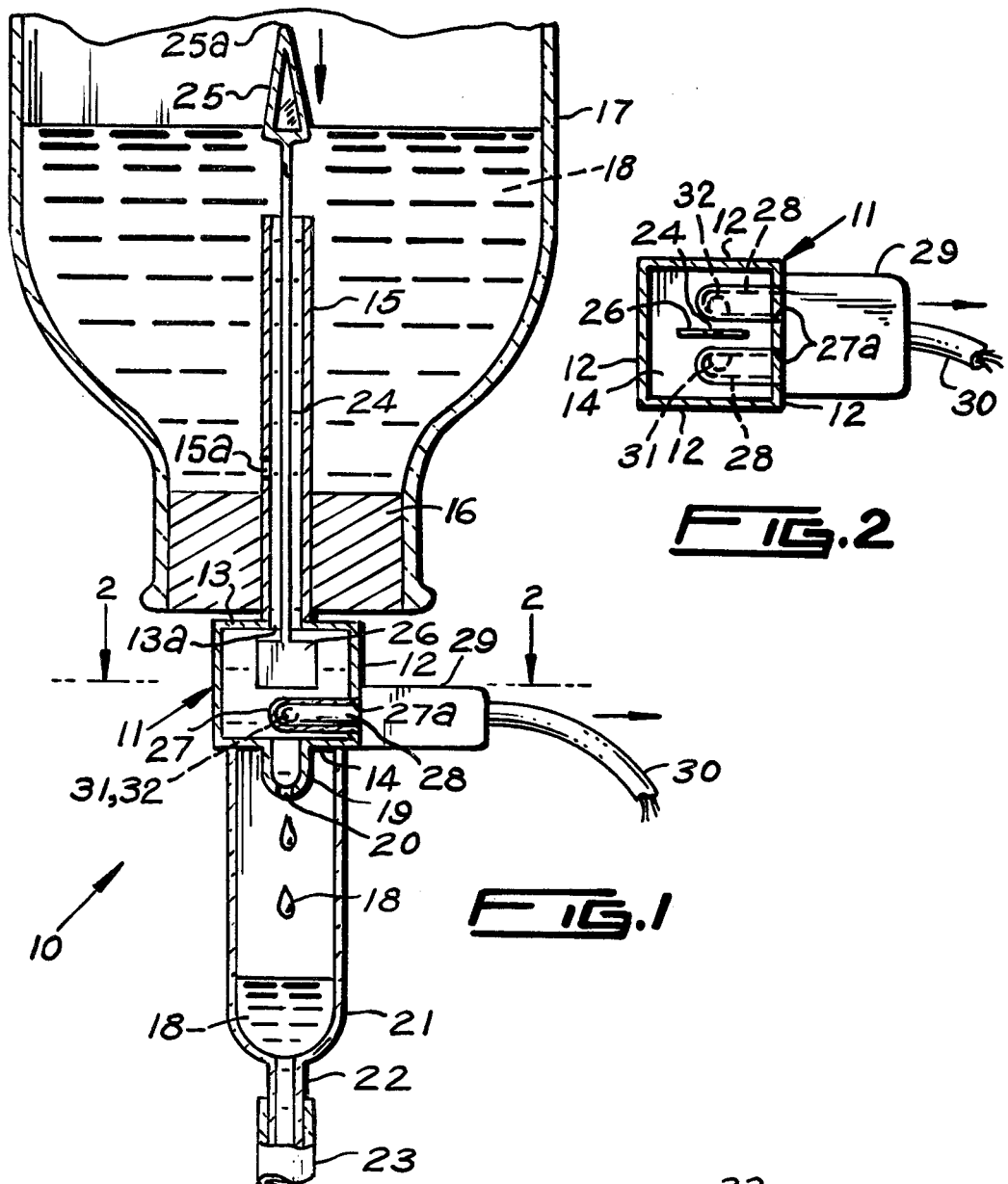
FIG.2
FIG.1
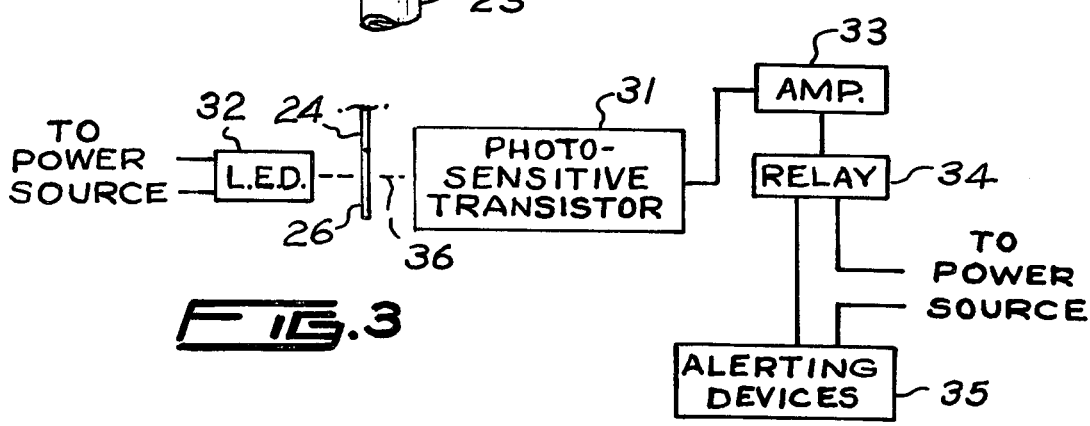
FIG.3

COMBINATION INTRA-VEINOUS FLOW-METER AND LOW LEVEL FLUID MECHANISM

This invention relates to intra-venous devices, and more particularly to a combination intra-venous flow-meter and low level fluid mechanism, which will alert hospital personnel to the ceasing of flow, of intra-venous fluid to a patient, from a bottle of the fluid, which is suspended from a bedside, etc.

Another object of this invention is to provide a combination intra-venous flow-meter, and low level fluid mechanism, which will employ the use of a float on the end of a stem which will have plate means on the opposite end, that when in the down position, will activate an alerting device, when the aforementioned fluid is being exhausted in the bottle.

Another object of this invention is to provide a combination intra-venous flow-meter and low level fluid mechanism, which will have the plate portion of the float stem, elevatable between a pair of transparent sleeves secured in an opaque housing, that the plate portion is carried in, and the transparent sleeves serve as a means for receiving the prongs of a sensing plug, that is secured to the alerting device.

A further object of this invention is to provide a combination intra-venous flow-meter and low level fluid mechanism, which will employ a light emitting diode in one of the prongs, and a photo-sensitive transistor in the other, the combination of the light emitting diode, the photo-sensitive transistor, and the plate portion of the float stem descending there-between, being the means of activating the alerting device, or devices.

A still further object of this invention is to provide a combination intra-venous flow-meter and low level fluid mechanism, which will employ a nipple on the bottom of the opaque housing, the nipple having a metering orifice in it, for metering the aforementioned fluid into a sump tube, that receives a flexible tube, and the stylus tube of the opaque housing will also include an orifice in its wall, above the bottle stopper, for low level fluid entry.

Other objects of the invention are to provide a combination intra-venous flow-meter and low level fluid mechanism, which will be simple in design, inexpensive to manufacture, rugged in construction and easy to use.

These and other objects of the invention, will be readily understood, upon a study of the specification and the accompanying drawing, in which:

FIG. 1 is a side view of the present invention, shown in section, and installed in a bottle of fluid, which is illustrated fragmentary and in elevation;

FIG. 2 is a cross-sectional view taken along the line 2—2 of FIG. 1 and

FIG. 3 is a block diagram of the electronic portion of the invention.

According to this invention, intra-venous flow-meter and low level fluid mechanism 10, is shown to include an opaque housing 11, of hollow and square configuration. Housing 11 is fabricated of side walls 12, a top wall 13, and a bottom wall 14. A tubular flow-meter stylus 15, is fixedly secured to top wall 13, over opening 13a therein, for a purpose, which hereinafter, will be described. Stylus 15 is received in stopper 16 of bottle 17, containing intra-venous fluid 18, and a nipple 19 integral of, and extending outwards from the bottom wall 14, of opaque housing 11, is provided with a metering orifice 20, from which, fluid 18 is dispensed by gravity means, into a transparent sump tube 21. Sump tube 21 is fixedly secured in a suitable manner, to bottom wall 14 of housing 11 at one end, and is provided with a neck 22, that is removably received within flexible polyethylene tube 23, that extends to a patient.

Stem 24 is freely elevatable, in the bore of stylus tube 15, and has secured fixedly, on one end, a hollow and conically configured float 25.

The point 25a of float 25, serves as tool means, for insertion of stylus tube 15, into bottle 17. A rectangular plate 26, integral of the opposite end of stem 24, is carried on the interior of opaque housing 11, within the fluid 18 therein, and fluid 18 feeds into the bore of stylus tube 15, and into housing 11. When fluid 18 is at a low level, it enters the orifice 15a of tube 15, so as to feed into housing 11.

A pair of parallel spaced apart and transparent sleeves 27, which are closed on one end, are fixedly secured, one each, in an opening 27a of one of the side walls 12 of opaque housing 11, and serve as receptacle means for the pair of prongs 28, of removable sensing plug 29, having cord 30. Plate 26 is so disposed, so as to descend down between sleeves 27. One of the prongs 28 of plug 29, has a photo-sensitive transistor 31 exposed towards, and in alignment with, a light emitting diode 32, in the other prong 28, and when fluid 18 reaches a low level in bottle 17, the float 25 will lower plate 26 between the sleeves 27, and the prongs 28, thus blocking the light from the light emitting diode 32.

Photo-sensitive transistor 31, as shown in FIG. 3, is coupled to amplifier 33, and amplifier 33 is coupled to a relay 34, and when the light is blocked by plate 24, relay 34 is activated, which will start the alerting device, or devices 35. The numerical character 36 in FIG. 3, indicates the light from the light emitting diode 32.

In use, the pointed float 25 is urged into the common stopper 16 of bottle 17, and it provides guide means, for easily entering the stylus tube 15, into the stopper 16. After securing tube 23 to neck 22 of sump tube 21, bottle 17 is then suspended in a manner common in the art. The cord 30 is secured in the usual manner, to the remotely located amplifier, relay 34 and alerting device 35 circuitry, that is housed in a suitable manner in the vicinity of the patient who is to receive the fluid 18. When the bottle 17 is depending, the prongs 28 of plug 29 are urged into the sleeves 27 of housing.

While various changes may be made in the detail construction, such changes will be within the spirit and scope of the present invention, as is defined by the appended claims.

What I claim is:

1. A combination intra-venous flow-meter and low level fluid mechanism, comprising, a hollow square housing of suitable material, a stylus tube fixedly secured at one end, over a central opening included in the top wall of said hollow square housing, and the opposite end of said stylus tube is removably received in the stopper of a bottle of intra-venous fluid, a stem freely and elevatably received in said stylus tube, a float fixedly secured at one end, to one end of said stem, for floatation on the intra-venous fluid level in its bottle, and a plate integral with the opposite end of said stem within said hollow square housing, in which the fluid travels, the bore of the stylus tube being the passageway means for fluid travel into said hollow square housing, and the end of said float is pointed, for easy insertion into the stopper of the bottle of intra-venous fluid.

2. A combination intra-venous flow-meter and low level fluid mechanism, comprising a hollow square housing of suitable material, a stylus tube fixedly secured at one end, over a central opening included in the top wall of said hollow square housing, and the opposite end of said stylus tube is removably received in the stopper of a bottle of intra-venous fluid, a stem freely and elevatably received in said stylus tube, a float fixedly secured at one end, to one end of said stem, for floatation on the intra-venous fluid level in its bottle, and a plate integral with the opposite end of said stem within said hollow square housing, in which the fluid travels, the bore of the stylus tube being the passageway means for fluid travel into said hollow square housing, and the end of said float is pointed, for easy insertion into the stopper of the bottle of intra-venous fluid, a pair of parallel spaced apart and transparent sleeves, closed on one end, extend inwardly, partially past the vertical axis of said hollow square housing, and the open end of each, is fixedly secured in an opening included in one of the side walls of said hollow square housing, and provides receptacle means for a pair of prongs of a sensing plug, and said pair of parallel spaced apart and transparent sleeves are disposed just above the bottom wall of said hollow square housing, and said bottom wall includes an orifice for passing fluid out of said hollow square housing.

3. A combination intra-venous flow-meter and low level fluid mechanism comprising a hollow square housing of suitable material, a stylus tube fixedly secured at one end, over a central opening included in the top wall of said hollow square housing, and the opposite end of said stylus tube is removably received in the stopper of a bottle of intra-venous fluid, a stem freely and elevatably received in said stylus tube, a float fixedly secured at one end, to one end of said stem, for floatation on the intra-venous fluid level in its bottle, and a plate integral with the opposite end of said stem within said hollow square housing, in which the fluid travels, the bore of the stylus tube being the passageway means for fluid travel into said hollow square housing, and the end of said float is pointed, for easy insertion into the stopper of the bottle of intra-venous fluid, and said plate is disposed on a plane centrally between a pair of parallel spaced apart and transparent sleeves, and when the intra-venous fluid attains a low level, the action of said float in the fluid, descends said plate between said pair of parallel spaced apart and transparent sleeves, for activating an alerting device, and an orifice in the wall of said stylus tube, spaced just above the bottle stopper, enables fluid to continue to enter said hollow square housing, after the fluid in the bottle passes the top end of said stylus tube.

4. A combination intra-venous flow-meter and low level fluid mechanism, comprising a hollow square housing of suitable material, a stylus tube fixedly secured at one end, over a central opening included in the top wall of said hollow square housing, and the opposite end of said stylus tube is removably received in the stopper of a bottle of intra-venious fluid, a stem freely and elevatably received in said stylus tube, a float fixedly secured at one end, to one end of said stem, for floatation on the intra-venous fluid level in its bottle, and a plate integral with the opposite end of said stem within said hollow square housing in which the fluid travels, the bore of the stylus tube being the passageway means for fluid travel into said hollow square housing, and the end of said float is pointed, for easy insertion into the stopper of the bottle of intra-venous fluid, one of a pair of prongs of a sensing plug, removably received in one of a pair of parallel spaced apart and transparent sleeves fixedly secured in a side wall of said hollow square housing, and said one of a pair of prongs, has fixedly secured therein, a light emitting diode, near the tip, and said light emitting diode is flush therewith, and faces towards one side of said plate in said hollow square housing, and the other of said pair of prongs in said sensing plug, has fixedly secured therein, a photo-sensitive transistor, near the tip, which is flush therewith and faces towards the opposite side of said plate, and the light from said light emitting diode is normally transmitted through the intra-venous fluid in said hollow square housing, to said photo-sensitive transistor, until said plate desends, by low fluid level in the bottle, which causes the transmitted light to said photo-sensitive transistor to be blocked, which activated an alerting device, and said photo-sensitive transistor is coupled to an amplifier that is coupled to a relay, and said relay is couple to said alerting device.

* * * * *